United States Patent [19]
Outwater

[11] Patent Number: 6,065,630
[45] Date of Patent: May 23, 2000

[54] SAPPHIRE TUBE PRESSURE VESSEL

[75] Inventor: John O. Outwater, Cambridge, Mass.

[73] Assignee: The United States of America as represented by the United States Department of Energy, Washington, D.C.

[21] Appl. No.: 09/206,957

[22] Filed: Dec. 8, 1998

[51] Int. Cl.[7] .................................................. B65D 45/00
[52] U.S. Cl. ..................... 220/327; 220/495.06; 220/662; 220/582
[58] Field of Search ..................................... 220/662, 664, 220/665, 327, 582, 23.87, 495.06, 676, 23.91, 62.21

[56] References Cited

U.S. PATENT DOCUMENTS

| | | | |
|---|---|---|---|
| 1,533,173 | 4/1925 | Egloff et al. | 220/582 |
| 3,080,201 | 3/1963 | Escola | 220/327 |
| 3,101,860 | 8/1963 | Flick | 220/327 |
| 3,141,008 | 7/1964 | Flick et al. | 220/327 |
| 3,205,764 | 9/1965 | Letter | 220/662 |
| 3,401,671 | 9/1968 | Axelrod et al. | 220/62.21 |
| 4,425,810 | 1/1984 | Simon et al. | 73/863.11 |
| 5,247,256 | 9/1993 | Marek | 324/321 |
| 5,977,772 | 11/1999 | Wand et al. | 324/321 |

OTHER PUBLICATIONS

"An Advanced In–Situ Sapphire Test Cell for Raman Spectroscopy within Aqueous Environments", D. M. Carey et al., *Applied Spectroscopy Journal*, vol. 52 (7), Jul. 1998.

*Primary Examiner*—Stephen Castellano
*Attorney, Agent, or Firm*—Virginia B. Caress; William R. Moser; Paul A. Gottlieb

[57] ABSTRACT

A pressure vessel is provided for observing corrosive fluids at high temperatures and pressures. A transparent Teflon bag contains the corrosive fluid and provides an inert barrier. The Teflon bag is placed within a sapphire tube, which forms a pressure boundary. The tube is received within a pipe including a viewing window. The combination of the Teflon bag, sapphire tube and pipe provides a strong and inert pressure vessel. In an alternative embodiment, tie rods connect together compression fittings at opposite ends of the sapphire tube.

7 Claims, 3 Drawing Sheets

SAPPHIRE TUBE PRESSURE VESSEL

This invention was made under a contract with the U.S. Department of Energy.

BACKGROUND OF THE INVENTION

1. Field of the Invention

The present invention relates to devices used to analyze corrosive fluids at high temperatures and high pressures.

2. Related Art

Optical test methods, such as Raman spectroscopy, require the use of transparent windows to separate the material to be analyzed from the test equipment. Diamond windows are frequently used in applications which involve corrosive fluids at elevated temperatures and pressures. However, diamond windows are expensive and fragile. As a result, substitutes such as quartz and sapphire windows have also been used. Quartz and sapphire windows are not optimal substitutes because they react with alkaline solutions at high temperatures and, as a result, have very short lives.

SUMMARY OF THE INVENTION

According to the invention, there is provided a pressure vessel for containing fluids to be optically analyzed which is inert to fluids over a large temperature range and is much cheaper than pressure vessels which contain diamond windows.

In accordance with a first embodiment of the invention, a pressure vessel for observing corrosive fluids at high temperatures and pressures, or items immersed in the corrosive fluid, is provided which comprises: a sapphire tube having at least one opening; a transparent polytetrafluoroethylene bag, preferably sealed on all sides and formed into a U-tube, located within the sapphire tube for holding a corrosive fluid; and a first compression fitting sealing the at least one opening.

In a preferred implementation of the first embodiment, the pressure vessel further includes a plug inserted into the first compression fitting for facilitating entry and removal of the corrosive fluid.

Advantageously, the pressure vessel includes a pipe having a window, the sapphire tube is located within the pipe. The pipe acts as a restraint.

It is also preferred that the at least one opening comprises openings at opposite ends of the sapphire tube and the first compression fitting and a second compression fitting seal each of the openings. Advantageously, tie rods connect the first and second compression fittings together.

In accordance with a second embodiment of the invention, a pressure vessel for observing corrosive fluids at high temperatures and pressures is provided which comprises: a sapphire tube for holding a corrosive fluid and having first and second openings at opposite ends thereof; first and second compression fittings for respectively sealing the first and second openings located at opposite ends of the sapphire tube; and tie rods for connecting the compression fittings together.

Other features and advantages of the invention will be set forth in, or apparent from, the following detailed description of the preferred embodiments of the invention.

DESCRIPTION OF THE PREFERRED EMBODIMENTS

Figure 1:
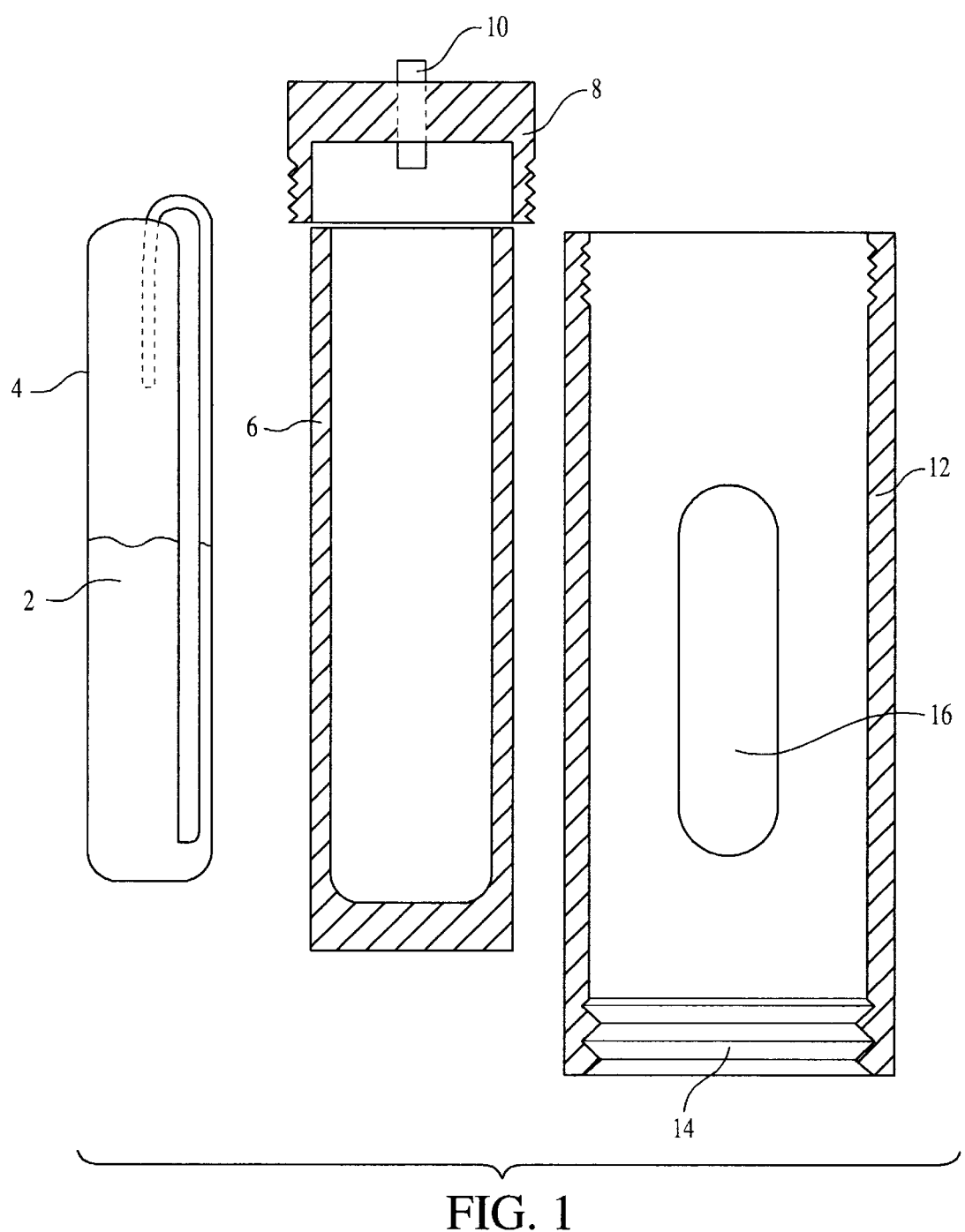
FIG. 1 is an exploded side elevation view, partially in cross section, of the components forming a pressure vessel in accordance with a first preferred embodiment of the invention.

Referring to FIG. 1, there is shown components of the pressure vessel in accordance with a first preferred embodiment of the invention. Fluid to be analyzed, which is generally denoted 2, is placed within a Teflon (polytetrafluoroethylene) bag 4. The Teflon bag 4 is fabricated to be thin enough to be transparent. The Teflon bag 4 is also closed at the top to prevent excessive evaporation and is formed into a U-tube, as shown, in order to prevent fluid from seeping out.

When the pressure vessel is heated in a furnace, a small amount of fluid 2 evaporates to self pressurize the Teflon bag 4 and the internal volume of a sapphire tube 6. In operation, the furnace must be kept a few degrees hotter at the top than at the bottom to prevent refluxing. In a preferred embodiment, the Teflon bag 4 is formed from heat-shrink tubing with a 0.003 inch wall. Teflon is one of the most inert substances available and will not erode over time.

The Teflon bag 4 is placed within a transparent and colorless sapphire tube 6. A compression fitting 8 seals the sapphire tube 6. The compression fitting 8 is preferably a Conax fitting with a Graphoil sealant (not shown). An axial-compression seal may also be used. However, a circumferential seal has the advantage of reducing stress concentrations on the sapphire tube 6, thereby reducing the chance of the tube failing. The compression fitting 8 contains a plug 10 for allowing access to the interior of the sapphire tube 6. The sapphire tube 6 forms a pressure boundary between the atmosphere and the fluid 2 to be analyzed. The pressure inside the Teflon bag 4 is kept at the same pressure as the region within the sapphire tube 6 and outside the Teflon bag 4.

The sapphire tube 6 is placed within a pipe 12 for restraint. The pipe 12 is sealed at the top with compression fitting 8 and at the bottom with a screw-in plug 14. The sapphire tube 6 and fluid 2 to be analyzed are viewed through a window 16.

Figure 2:
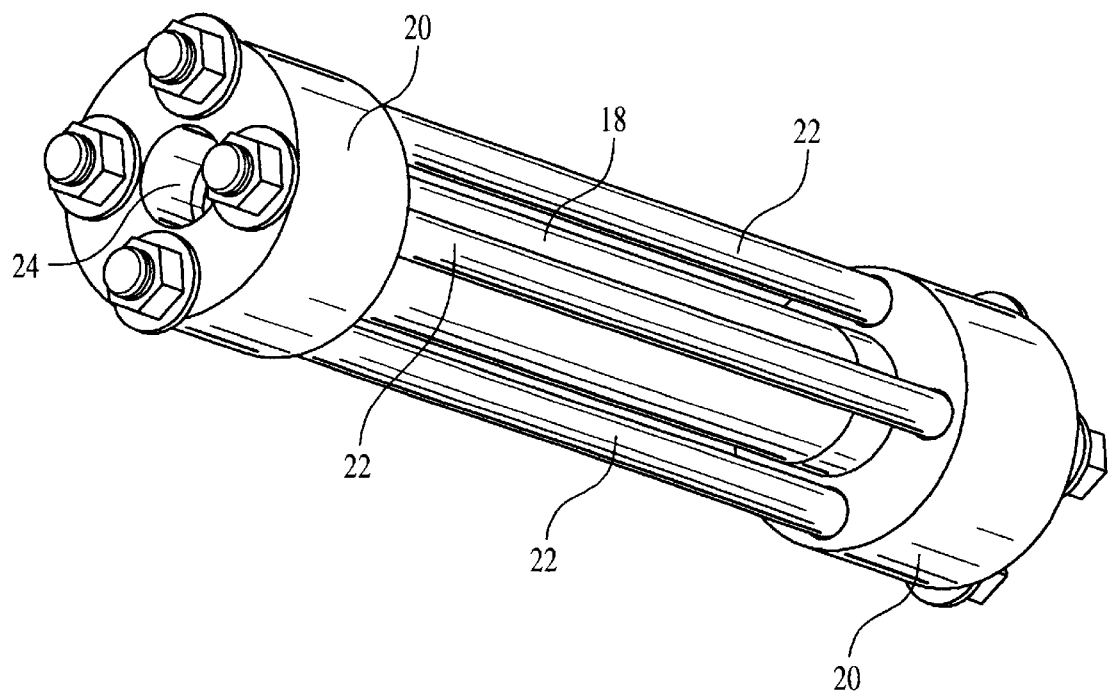
FIG. 2 is a side elevation view of a pressure vessel in accordance with a second preferred embodiment of the invention.
Figure 2A:
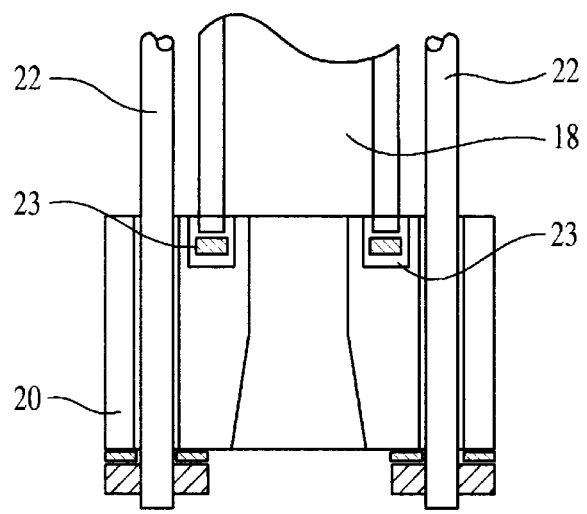
FIG. 2A is a cross sectional view of the pressure vessel in accordance with the second preferred embodiment of the invention and including an axial seal arrangement.

An alternative embodiment of the invention is shown in FIGS. 2 and 2A. A sapphire tube 18 has openings at both ends and these openings are capped at both ends with end caps 20. A Teflon bag 4 corresponding to that discussed above may be inserted into the sapphire tube 18 in the same manner as shown in FIG. 1, if the fluid to be analyzed is of a type that will corrode sapphire. The Teflon bag 4 starts to decompose at a temperature which is lower than the decomposition temperature of the other components. Therefore, the use of the Teflon bag 4 should be avoided at temperatures above approximately 290° C.

Tie rods 22 connect the end caps 20 together. Titanium tie rod material is preferred to match the thermal expansion of the sapphire tube 18. Graphoil gaskets 23 are shown in FIG. 2A. The Graphoil gaskets 23 are compressed when the tie rods 22 are secured to the end caps 20 and form a seal. Each end cap 20 has an entry hole 24 which facilitates the insertion of liquids and gases into the sapphire tube 18. The entry holes 24 may contain fittings for inserting electrodes, thermocouples or other sensing elements into the sapphire tube 18. Once the fluid to be analyzed is inserted into the sapphire tube 18, the entry holes 24 are plugged. In an alternative embodiment, the entry holes 24 are not plugged and the fluid to be analyzed is observed as it flows through the sapphire tube 18. The pressure vessel shown in FIGS. 2 and 2A is capable of withstanding approximately 5,000 psi at room temperature.

Figure 3:
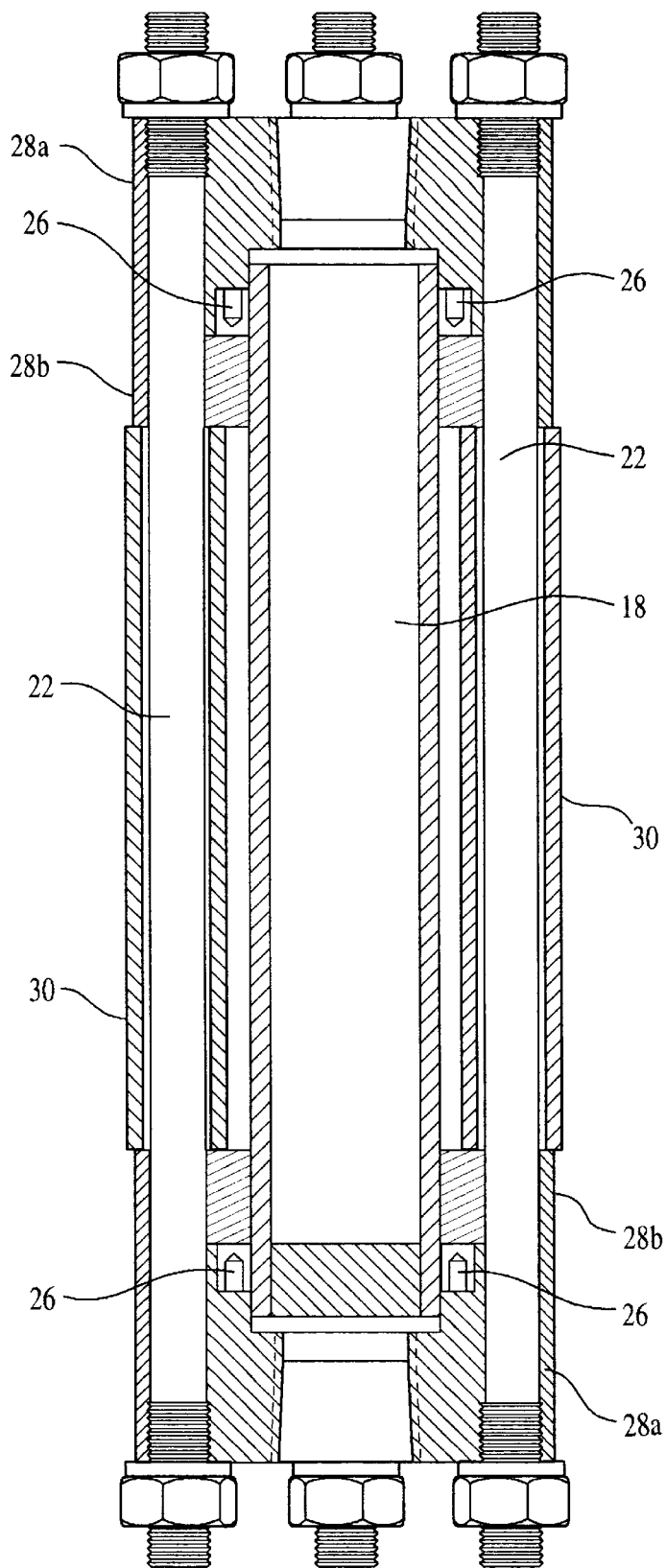
FIG. 3 is a cross-sectional side elevation view of a pressure vessel in accordance with a third preferred embodiment of the invention.

Another alternative embodiment of the invention is shown in FIG. 3. The embodiment shown in FIG. 3 includes circumferential seal gaskets 26. Each end cap 28 includes a first section 28a and a second section 28b. The tie rods 22 pass through rigid tubing 30 which is in contact with the second sections 28b of the end caps. When the tie rods 22 are secured to the first sections of the end caps 28a, the circumferential seal gaskets 26 are compressed between sections 28a and 28b of the end caps and form a seal against the sapphire tube 18. The seal gaskets 26 can be compressed Graphoil seals (for very high temperatures and lower pressures) or, preferably, spring-loaded C-ring seals (for very high pressures and lower temperatures).

Although the invention has been described in detail with respect to preferred embodiments thereof, it will be apparent to those skilled in the art that variations and modifications can be effected in these embodiments without departing from the spirit and scope of the invention.

We claim:

1. A pressure vessel for observing corrosive fluids at high temperatures and pressures, said pressure vessel comprising:

a sapphire tube for holding a corrosive fluid and having first and second openings at opposite ends thereof;

first and second compression fittings for respectively sealing said first and second openings located at opposite ends of said sapphire tube; and tie rods for connecting said compression fittings together.

2. A pressure vessel for observing corrosive fluids at high temperatures and pressures, said pressure vessel comprising:

a sapphire tube having at least one opening therein;

a transparent polytetrafluoroethylene bag located within said sapphire tube for holding a corrosive fluid; and a first compression fitting sealing said at least one opening.

3. The pressure vessel according to claim 2, further including a plug inserted into said first compression fitting for facilitating entry and removal of the corrosive fluid and sensing elements.

4. The pressure vessel according to claim 2, further including a pipe having a window, said sapphire tube being located within said pipe.

5. The pressure vessel according to claim 2, wherein said at least one opening comprises openings at opposite ends of said sapphire tube and wherein said first compression fitting and a second compression fitting seal each of said openings.

6. The pressure vessel according to claim 5, further including tie rods for connecting said first and second compression fittings together.

7. The pressure vessel according to claim 2, wherein said transparent polytetrafluoroethylene bag is sealed on all sides and formed into a U-tube.

* * * * *